United States Patent [19]

Bank et al.

[11] Patent Number: 5,756,795
[45] Date of Patent: May 26, 1998

US005756795A

[54] UNSATURATED ACCELERATORS FOR HYDROSILATION

[75] Inventors: Howard Marvin Bank, Freeland; Aroop Kumar Roy, Midland, both of Mich.

[73] Assignee: Dow Corning Corporation, Midland, Mich.

[21] Appl. No.: 775,229

[22] Filed: Dec. 30, 1996

[51] Int. Cl.$^6$ ........................................... C07F 7/08
[52] U.S. Cl. ........................................... 556/479
[58] Field of Search ........................................... 556/479

[56] References Cited

U.S. PATENT DOCUMENTS

| | | | |
|---|---|---|---|
| 2,823,218 | 2/1958 | Speier et al. | 260/448.2 |
| 3,220,972 | 11/1965 | Lamoreaux | 260/46.5 |
| 3,419,593 | 12/1968 | Willing | 260/448.2 |
| 4,578,497 | 3/1986 | Onopchenko et al. | 556/479 |
| 5,175,325 | 12/1992 | Brown et al. | 556/9 |
| 5,359,111 | 10/1994 | Kleyer et al. | 556/479 |
| 5,563,287 | 10/1996 | Roy | 556/479 |
| 5,565,596 | 10/1996 | Roy | 556/479 |

*Primary Examiner*—Paul F. Shaver
*Attorney, Agent, or Firm*—Melvin D. Fletcher

[57] ABSTRACT

A hydrosilation process where a silicon hydride is reacted with an unsaturated reactant in the presence of a platinum catalyst and an accelerator selected from the group consisting of 1,7-octadiyne, 1,5-hexadiyne, cyclooctadiene, 5-vinyl-2-norbornene, 4-vinyl-1-cyclohexene, 2,5-bis(t-butylperoxy)-2,5-dimethylhexane, furan, 4H-Pyran-4-one, cis-4,7-dihydro-1,3-dioxepin, maleic anhydride, and dimethyldiallylmalonate. The accelerators are especially useful for facilitating the hydrosilation of unsaturated reactants where the unsaturation is in the internal portion of the reactant's structure, for example, as in cyclopentene and cyclohexene.

19 Claims, No Drawings

UNSATURATED ACCELERATORS FOR HYDROSILATION

BACKGROUND OF THE INVENTION

This invention relates to a hydrosilation process where a silicon hydride is reacted with an unsaturated reactant in the presence of a platinum catalyst and an accelerator selected from a group consisting of 1,7-octadiyne, 1,5-hexadiyne, cyclooctadiene, 5-vinyl-2-norbornene, 4-vinyl-1-cyclohexene, 2,5-bis(t-butylperoxy)-2,5-dimethylhexane, furan, 4H-Pyran-4-one, cis-4,7-dihydro-1,3-dioxepin, maleic anhydride, and dimethyldiallylmalonate. The accelerators are especially useful for facilitating the hydrosilation of unsaturated reactants where the unsaturation is in the internal portion of the reactant's structure, for example, as in cyclopentene and cyclohexene.

It is known in the art to produce organosilicon compounds by reacting a silicon hydride containing compound with an unsaturated organic compound in the presence of a catalyst. This reaction is commonly referred to as hydrosilation or hydrosilylation. Typically the catalyst is platinum metal on a support, a platinum compound generally in a solvent, or a platinum complex.

Speier et al., U.S. Pat. No. 2,823,218, teach a method for the production of organosilicon compounds by reacting an Si—H with a compound containing aliphatic carbon atoms linked by multiple bonds in the presence of chloroplatinic acid. Lamoreaux, U.S. Pat. No. 3,220,972, teaches a similar process, however the catalyst is a reaction product of chloroplatinic acid.

One of the major problems known in the art with hydrosilation reactions is the de-activation of the catalyst prior to the completion of the reaction. One method for reactivation of the catalyst has been to expose the reaction mixture to oxygen. For example, Onopchenko et al., U.S. Pat. No. 4,578,497, teach the use of an oxygenated platinum containing catalyst for use in hydrosilating alkylsilanes. Kleyer et al., U.S. Pat. No. 5,359,111, disclose a method for controlling hydrosilation reaction mixtures by controlling the solution concentration of oxygen in the reaction mixture, relative to the platinum present in the reaction mixture.

In addition to the problem of de-activation of the platinum catalyst, hydrosilation processes taught in the art are not particularly effective in hydrosilating internal unsaturated bonds in organic molecules. The present inventors have unexpectedly discovered that 1,7-octadiyne, 1,5-hexadiyne, cyclooctadiene, 5-vinyl-2-norbornene, 4-vinyl-1-cyclohexene, 2,5-bis(t-butylperoxy)-2,5-dimethylhexane, furan, 4H-Pyran-4-one, cis-4,7-dihydro-1,3-dioxepin, maleic anhydride and dimethyldiallylmalonate, act as accelerators for platinum catalyzed hydrosilation processes. These accelerators can improve yield of the process in the presence or absence of oxygen and are particularly effective in facilitating the hydrosilation of internal unsaturated bonds of organic molecules.

SUMMARY OF INVENTION

The present invention is a hydrosilation process where a silicon hydride is reacted with an unsaturated reactant in the presence of a platinum catalyst and an accelerator selected from the group consisting of 1,7-octadiyne, 1,5-hexadiyne, cyclooctadiene, 5-vinyl-2-norbornene, 4-vinyl-1-cyclohexene, 2,5-bis(t-butylperoxy)-2,5-dimethylhexane, furan, 4H-Pyran-4-one, cis-4,7-dihydro-1,3-dioxepin, maleic anhydride and dimethyldiallylmalonate. The accelerators are especially useful for the hydrosilation of unsaturated reactants where the unsaturation is in the internal portion of the compound's structure, for example, as in cyclopentene and cyclohexene. The accelerators are effective in the absence of oxygen activation of the platinum catalyst and are synergetic with oxygen activation of platinum catalyst.

DESCRIPTION OF INVENTION

The invention is a hydrosilation process where a silicon hydride is reacted with an unsaturated reactant in the presence of a platinum catalyst and an accelerator. The hydrosilation process comprises: contacting (A) a silicon hydride described by formula $R^1_a H_b SiX_{4-a-b}$ where each $R^1$ is independently selected from the group consisting of alkyls comprising one to about 20 carbon atoms, cycloalkyls comprising about four to about 12 carbon atoms, and aryls; each X is an independently selected halogen; $a=0$ to 3, $b=1$ to 3, and $a+b=1$ to 4; and (B) an unsaturated reactant selected from the group consisting of (i) substituted and unsubstituted unsaturated organic compounds,
  (ii) silicon compounds comprising substituted or unsubstituted unsaturated organic substituents, and
  (iii) mixtures of (i) and (ii);

in the presence of a platinum catalyst selected from the group consisting of platinum compounds and platinum complexes, and an accelerator selected from the group consisting of 1,7-octadiyne, 1,5-hexadiyne, cyclooctadiene, 5-vinyl-2-norbornene, 4-vinyl-1-cyclohexene, 2,5-bis(t-butylperoxy)-2,5-dimethylhexane, furan, 4H-Pyran-4-one, cis-4,7-dihydro-1,3-dioxepin, maleic anhydride, and dimethyldiallylmalonate.

The contacting of the silicon hydride with the unsaturated reactant can be effected in standard type reactors for conducting hydrosilation processes. The contact and reaction may be run as a continuous, semi-continuous, or batch process.

Silicon hydrides which are useful in the present process are described by formula $R^1_a H_b SiX_{4-a-b}$, where each $R^1$ is independently selected from the group consisting of alkyls comprising one to 20 carbon atoms, cycloalkyls comprising four to 12 carbon atoms, and aryls; $a=0$ to 3, $b=1$ to 3, and $a+b=1$ to 4. $R^1$ can be a substituted or unsubstituted alkyl, cycloalkyl, or aryl as described. It is preferred that each $R^1$ be independently selected from a group consisting of alkyls comprising about one to six carbon atoms. Even more preferred is when each $R^1$ is methyl.

In the formula describing the silicon halide each X is independently selected halogen and preferably X is chlorine.

Examples of silicon hydrides which may be useful in the present process include trimethylsilane, dimethylsilane, triethylsilane, dichlorosilane, trichlorosilane, methyldichlorosilane, dimethylchlorosilane, ethyldichlorosilane, cyclopentyldichlorosilane, methylphenylchlorosilane, and (3,3,3-trifluoropropyl) dichlorosilane. A preferred silicon hydride is selected from the group consisting of methyldichlorosilane and dichlorosilane.

The silicon hydride is contacted with an unsaturated reactant selected from the group consisting of (i) substituted and unsubstituted unsaturated organic compounds, (ii) silicon compounds containing substituted and unsubstituted unsaturated organic substituents, and (iii) mixtures of (i) and (ii). For the purposes of this invention, "unsaturated" means that the compound contains at least one carbon-carbon double bond.

More specific examples of the unsaturated reactants useful in the process include unsubstituted cycloalkene compounds comprising at least four carbon atoms, substituted cycloalkene compounds comprising at least four carbon atoms, linear alkene compounds comprising about two to 30 carbon atoms, branched alkene compounds comprising four to about 30 carbon atoms, and mixtures of two or more of any of the above.

The substituted and unsubstituted cycloalkene compounds useful in the process are those containing one or more unsaturated carbon-carbon bonds in the ring. The unsubstituted cycloalkene compounds may be, for example, cyclobutene, cyclopentene, cyclohexene, cycloheptene, cyclooctene, cyclopentadiene, 1,3-cyclohexadiene, and 1,3,5-cycloheptatriene. Substituted unsaturated compounds useful in the present invention may be, for example, 3-methylcyclopentene, 3-chlorocyclobutene, 4-phenylcyclohexene, and 3-methylcyclopentadiene. The preferred cycloalkene compounds are cyclohexene and cyclopentene, with cyclohexene being the most preferred.

Other unsaturated organic compounds useful in the process are linear and branched alkene compounds including, for example, compounds with terminal unsaturation such as 1-hexene and 1,5-hexadiene, compounds with internal unsaturation such as trans-2-hexene, and unsaturated aryl containing compounds such as styrene and alpha-methylstyrene.

The unsaturated reactants may also contain halogen, oxygen in the form of acids, anhydrides, alcohols, esters, and ethers, and nitrogen. Two or more of the above described unsaturated organic compounds may be used in the present process.

The unsaturated organic compounds containing halogen may include, for example, vinyl chloride, allyl chloride, allyl bromide, allyl iodide, allyl bromide, methallyl chloride, trichloroethylene, tetrachloroethylene, tetrafluoroethylene, chloroprene, vinylidene chloride, and dichlorostyrene.

Suitable unsaturated organic compounds comprising oxygen can include, for example, ethers such as allyl and vinyl ethers; alcohols such as allyl alcohol (vinyl carbinol), methylvinylcarbinol and ethynyldimethyl-carbinol; acids such as acrylic, methacrylic, vinylacetic, oleic, sorbic, and linolenic; and esters such as vinyl acetate, allyl acetate, butenyl acetate, allyl stearate, methylacrylate, ethylcrotonate, diallyl succinate and diallyl phthalate. Suitable nitrogen containing unsaturated organic compounds include, for example, indigo, indole, acrylonitrile, and allyl cyanide.

Specifically included within the definition of unsaturated organic compounds are those substituted by organofunctional moieties such as $CH_2=CHCH_2OC(O)C(CH_3)=CH_2$,
$CH_2=CHCH_2NHCH_2CH_2NH_2$, $CH_2=CHCH_2NH_2$,

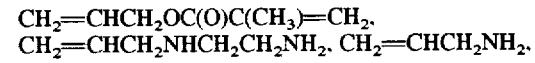

$CH_2=CHCH_2SH$, $CH_2=CHSi\{O(CH_2)_2OCH_3\}_3$,
$CH_2=CHCH_2N(HCl)HCH_2CH_2NHCH_2(C_6H_4)CH=CH_2$,
and other similar such compounds.

The unsaturated organic compound can be a silicon compound containing substituted and unsubstituted organic substituents as described by, for example, formulas $(CH_2=CH(CH_2)_g)_hR^1{}_iSi(OR^1)_{4-h-i}$ and $(CH_2=CH(CH_2)_g)_hR^1{}_iSiCl_{4-h-i}$ where $R^1$ is as previously described, $g=0$ to 12, $h=1$ to 3, $i=0$ to 3, and $h+i=1$ to 4.

Prior to contact of the silicon hydride with the unsaturated reactant, it may be preferable to treat or purify the unsaturated reactant. Methods useful for treating or purifying the unsaturated reactants are those known in the art for treating or purifying unsaturated organic compounds and include but are not limited to distillation and treatment with an adsorbent such as activated alumina or molecular sieves.

The relative amounts of silicon hydride and unsaturated reactant used in the present process can be varied within wide limits. Although one unsaturated carbon-carbon linkage per silicon bonded hydrogen atom is stoichiometric, there is no requirement that the process be run under stoichiometric conditions. Generally, it is preferred that the process be run with a stoichiometric excess of silicon hydride. Preferred is when the process is run with about 0.1 to ten percent stoichiometric excess of silicon hydride.

The silicon hydride and unsaturated reactant are contacted in the presence of a catalyst selected from a group consisting of platinum compounds and platinum complexes. Any platinum containing material which effects the reaction between the silicon hydride and an unsaturated carbon-carbon bond of the unsaturated organic compound is useful in the present invention. Examples of platinum catalysts useful in the present process are described, for example, in Onopchenko, U.S. Pat. No. 4,578,497; Lamoreaux, U.S. Pat. No. 3,220,972; and Speier, U.S. Pat. No. 2,823,218; and Willing, U.S. Pat. No. 3,419,593 all of which are hereby incorporated herein by reference.

The catalyst can be, for example, chloroplatinic acid, chloroplatinic acid hexahydrate, Karstedt's catalyst (i.e. a complex of chloroplatinic acid with sym-divinyltetramethyldisiloxane), dichlorobis(triphenylphosphine)-platinum(II), cis-dichlorobis(acetonitrile)-platinum(II), dicarbonyldichloroplatinum(II), platinum chloride, platinum oxide and platinum vinylsiloxane complexes such as a neutralized complex of platinum dichloride with sym-divinyltetramethyldisiloxane.

A preferred platinum catalyst is selected from the group consisting of chloroplatinic acid, chloroplatinic acid hexahydrate, and platinum vinylsiloxane complexes such as a neutralized complex of chloroplatinic acid or platinum dichloride with sym-divinyltetramethyldisiloxane. An example of a platinum catalyst is described in Brown et al., U.S. Pat. No. 5,175,325.

Generally, those concentrations of catalyst which provide about one mole of platinum per billion moles of unsaturated carbon-carbon bonds added to the process by the unsaturated reactant may be useful in the present process. Concentrations of catalyst providing as high as about one mole of platinum per one thousand moles of unsaturated carbon-carbon bonds added to the process by the unsaturated reactant may be useful. Higher concentrations of platinum may be used if desired. A preferred concentration of platinum catalyst is that providing about one to 1000 moles of platinum per $1\times10^6$ moles of unsaturated carbon-carbon bonds provided to the process by the unsaturated reactant.

The catalyst may be dissolved in a solvent for ease of handling and to facilitate measuring the small amounts typically needed. Suitable solvents include, for example, non-polar hydrocarbon solvents such as benzene, toluene, and xylene and polar solvents such as alcohols, glycols, and esters.

The process is carried out in the presence of accelerators selected from the group consisting of 1,7-octadiyne, 1,5-hexadiyne, cyclooctadiene, 5-vinyl-2-norbornene, 4-vinyl-1-cyclohexene, 2,5-bis(t-butylperoxy)-2,5-dimethylhexane, furan, 4H-Pyran-4-one, cis-4,7-dihydro-1,3-dioxepin, maleic anhydride, and dimethyldiallylmalonate. The above listed accelerators are commercially available.

An effective concentration of the selected accelerator is added to the present process, where an effective concentration is one that facilitates initiation of the reaction between the silicon hydride and the unsaturated organic compound, accelerates the rate of the reaction, or reduces loss of reactivity of the catalyst in the process. A useful effective concentration of the accelerator is generally within a range of about 0.01 to 20 weight percent of the weight of the unsaturated reactant. Preferred is when the accelerator is about 0.1 to ten weight percent of the weight of the unsaturated reactant.

The presence of oxygen during conduct of the present process can enhance reaction parameters such as the reaction rate and selectivity of addition when the solution concentration of oxygen is controlled relative to platinum catalyst in the reaction mixture. The oxygen can be added into the reaction mixture by bubbling it into one of the reactants or by bubbling it into the reaction mixture. Feeding the oxygen into the vapor space of the reactor or by purging the reactor system with oxygen may also be used, but may not be as effective due to mass transfer considerations.

The effective amount of oxygen to be added to the present process will be dependent upon such factors as the operating conditions, the reactants, and the amount of catalyst present. It is preferred to introduce the oxygen into the process combined with an inert gas at an oxygen level of parts per million to about 20 weight percent, based on the combined weights of the oxygen and inert gas. More preferred is when the oxygen is diluted in an inert gas to about 0.1 to 40 weight percent. The inert gas can be, for example, nitrogen or argon. Typically, the preferred amount of oxygen to be added to the process can be determined by monitoring the rate of reaction and by-product formation. A process for adding oxygen to a hydrosilation process is described, for example, in Kleyer et al., U.S. Pat. No. 5,359,111, which is hereby incorporated by reference as a further description of the way oxygen may be used in the present process.

The following examples are provided to illustrate the present invention. These examples are not intended to limit the claims herein.

EXAMPLE 1

A stock mixture was prepared in an argon purged and blanketed bottle. The stock mixture comprised seven molar percent excess of methyldichlorosilane in cyclohexene which had been treated with 13× molecular sieves. About $6\times10^{-5}$ moles of platinum, as a complex prepared by the reaction of $PtCl_2$ with sym-divinyltetramethyldisiloxane, per mole of cyclohexene was added to the stock mixture. A 2 ml aliquot of this catalyzed stock solution was then transferred to argon-purged glass tubes and the accelerators as listed in Table 1 were added to individual tubes at a concentration of 0.4 volume percent. The tubes were cooled, heat sealed under an argon purge, and heated at 80° C. for three hours. At the end of three hours the tubes were cooled and the contents analyzed by gas chromatography using a thermal conductivity detector (GC-TC). The results of this analysis are reported in Table 1 as the normalized area percent of cyclohexylmethyldichlorosilane ($C_HMeSiCl_2$) under the GC-TC trace minus the area percent of cyclohexene as 100%.

TABLE 1

| Accelerator | $C_HMeSiCl_2$ Normalized Area % |
|---|---|
| None | 60.8 |
| Cyclooctadiene | 91.2 |
| MeViSi(MBO)$_2$ | 99.1 |
| None | 61.7 |
| 1,5-Hexadiyne | 77.8 |
| Furan | 92.0 |
| 2-Methyl-1-hexen-3-yne | 86.4 |
| 4H-Pyran-4-one | 95.5 |
| None | 52.5 |
| 1,7-Octadiyne | 96.5 |
| Dimethyldiallylmalonate | 70.1 |
| None | 66.3 |
| Cis-4,7-Dihydro-1,3-dioxepin | 79.4 |
| None | 41.2 |
| 5-vinyl-2-norbornene | 93.7 |
| 4-vinyl-1-cyclohexene | 80.8 |
| Maleic anhydride | 90.4 |

EXAMPLE 2

A stock mixture was prepared in an argon purged and blanketed bottle. The stock mixture comprised seven molar percent excess of methyldichlorosilane in cyclohexene which had been treated with 13× molecular sieves. About $6.9\times10^{-5}$ moles of a platinum-containing complex which is the neutralized reaction product of chloroplatinic acid and symdivinyltetramethyldisiloxane, per mole of cyclohexene was added to the stock mixture. A 2 ml aliquot of this catalyzed stock solution was transferred to a argon-purged glass tube and the accelerator 2,5-bis(t-butylperoxy)2,5-dimethylhexane was added to the tube at a concentration of 1 volume percent. The tube was cooled, heat sealed under an argon purge, and heated at 80° C. for three hours. At the end of three hours the tube was cooled and the contents analyzed by gas chromatography using a thermal conductivity detector (GC-TC). The results of this analysis in area percent are 7.0% cyclohexene, 4.1% methyldichlorosilane, and 82.2% cyclohexylmethyldichlorosilane under the GC-TC trace.

We claim:

1. A hydrosilation process comprising reacting:
   (A) a silicon hydride described by formula $R^1{}_aH_bSiX_{4-a-b}$, where each $R^1$ is independently selected from the group consisting of alkyls comprising one to about 20 carbon atoms, cycloalkyls comprising about four to about 12 carbon atoms, and aryls; each X is an independently selected halogen; a=0 to 3, b=1 to 3, and a+b=1 to 4; and
   (B) an unsaturated reactant selected from the group consisting of
   (i) substituted and unsubstituted unsaturated organic compounds,
   (ii) silicon compounds containing substituted or unsubstituted unsaturated organic substituents, and
   (iii) mixtures of (i) and (ii);
   in the presence of a platinum catalyst selected from the group consisting of platinum compounds and platinum complexes, and an accelerator selected from the group consisting of 1,7-octadiyne, 1,5-hexadiyne, 5-vinyl-2-norbornene, 2,5-bis(t-butylperoxy)-2,5-dimethylhexane, furan, 4H-pyran-4-one, maleic anhydride, cis-4,7-dihydro-1,3-dioxepin and dimethyldiallylmalonate.

2. A process according to claim 1, where the silicon hydride is selected from the group consisting of methyldichlorosilane and dichlorosilane.

3. A process according to claim 1, where the unsaturated reactant is selected from the group consisting of cyclohexene and cyclopentene.

4. A process according to claim 1, where the unsaturated reactant is cyclohexene.

5. A process according to claim 1, where the platinum catalyst is selected from the group consisting of chloroplatinic acid, chloroplatinic acid hexahydrate, and platinum vinylsiloxane complexes.

6. A process according to claim 1, where the accelerator is 1-7-octadiyne.

7. A process according to claim 1, where the accelerator is 5-vinyl-2-norbornene.

8. A process according to claim 1, where the accelerator is 2,5-bis(t-butylperoxy)-2,5-dimethylhexane.

9. A process according to claim 1, where the accelerator is furan.

10. A process according to claim 1, where the accelerator is 4H-Pyran-4-one.

11. A process according to claim 1, where the accelerator is cis-4,7-dihydro-1,3-dioxepin.

12. A process according to claim 1, where the silicon hydride is methyldichlorosilane, the unsaturated reactant is cyclohexene, and the accelerator is 1,7-octadiyne.

13. A process according to claim 1, where the silicon hydride is methyldichlorosilane, the unsaturated reactant is cyclohexene, and the accelerator is 5-vinyl-2-norbornene.

14. A process according to claim 1, where the silicon hydride is methlydichlorosilane, the unsaturated reactant is cyclohexene, and the accelerator is 2,5-bis(t-butylperoxy)-2,5-dimethylhexane.

15. A process according to claim 1, where the silicon hydride is methlydichlorosilane, the unsaturated reactant is cyclohexene, and the accelerator is furan.

16. A process according to claim 1, where the silicon hydride is methlydichlorosilane, the unsaturated reactant is cyclohexene, and the accelerator is 4H-Pyran-4-one.

17. A process according to claim 1, where the silicon hydride is methlydichlorosilane, the unsaturated reactant is cyclohexene, and the accelerator is cis-4,7-dihydro-1,3-dioxepin.

18. A process according to claim 1, where the concentration of the accelerator is within a range of about 0.01 to 20 weight percent of the weight of the unsaturated reactant.

19. A process according to claim 1, where the silicon hydride is selected from the group consisting of methyldichlorosilane and dichlorosilane, and the unsaturated reactant is selected from the group consisting of cyclohexene and cyclopentene, and the accelerator is selected from the group consisting of 1,7-octadiyne, 1,5-hexadiyne, 5-vinyl-2-norbornene, 2,5-bis(t-butylperoxy)-2,5-dimethylhexane, furan, 4H-Pyran-4-one, cis-4,7-dihydro-1,3-dioxepin, maleic anhydride and dimethyldiallylmalonate.

* * * * *